(12) United States Patent
Maruyama et al.

(10) Patent No.: US 10,937,333 B2
(45) Date of Patent: Mar. 2, 2021

(54) REHABILITATION SYSTEM

(71) Applicant: Seiko Epson Corporation, Tokyo (JP)

(72) Inventors: Yuya Maruyama, Kai (JP); Hideki Tanaka, Chino (JP)

(73) Assignee: Seiko Epson Corporation

( * ) Notice: Subject to any disclaimer, the term of this patent is extended or adjusted under 35 U.S.C. 154(b) by 303 days.

(21) Appl. No.: 15/785,790

(22) Filed: Oct. 17, 2017

(65) Prior Publication Data

US 2018/0108271 A1 Apr. 19, 2018

(30) Foreign Application Priority Data

Oct. 19, 2016 (JP) .............................. JP2016-204929

(51) Int. Cl.
*G09B 19/00* (2006.01)
*G06F 3/01* (2006.01)
(Continued)

(52) U.S. Cl.
CPC .......... *G09B 19/003* (2013.01); *A61B 5/0261* (2013.01); *A61B 5/0476* (2013.01); *A61B 5/0488* (2013.01); *A61B 5/1118* (2013.01); *A61B 5/1123* (2013.01); *A61B 5/1455* (2013.01); *A61B 5/4076* (2013.01); *A61B 5/486* (2013.01); *G02B 27/017* (2013.01);
(Continued)

(58) Field of Classification Search
None
See application file for complete search history.

(56) References Cited

U.S. PATENT DOCUMENTS 7,437,196 B2 * 10/2008 Wyler ................ A61N 1/36067
607/45
8,121,694 B2 * 2/2012 Molnar .............. A61B 5/04014
607/45
(Continued)

FOREIGN PATENT DOCUMENTS

JP          4618795 B2    1/2011
WO    WO-2016-002200 A1    1/2016
(Continued)

OTHER PUBLICATIONS

Giuliana Grimaldi; "Neurological Tremor: Sensors, Signal Processing and Emerging Applications"; 2010; https://www.ncbi.nlm.nih.gov/pmc/articles/PMC3244020/ (Year: 2010).*
(Continued)

*Primary Examiner* — Eddy Saint-Vil
*Assistant Examiner* — William D Ermlick
(74) *Attorney, Agent, or Firm* — Harness, Dickey & Pierce, P.L.C.

(57) ABSTRACT

A rehabilitation system includes: a brain activity measuring device which measures brain activity of a patient who carries out training based on a set amount of training; a motion measuring device which measures a motion state of a paralyzed site of the patient; a spasticity state determiner which determines a spasticity state based on the brain activity and the motion state; an updater which updates the amount of training based on a result of determination by the spasticity state determiner; and a presentation device which presents the updated amount of training to the patient.

2 Claims, 7 Drawing Sheets (51) Int. Cl.
*A61B 5/00* (2006.01)
*A61B 5/026* (2006.01)
*A61B 5/0476* (2006.01)
*A61B 5/0488* (2006.01)
*A61B 5/11* (2006.01)
*A61B 5/1455* (2006.01)
*G09B 5/02* (2006.01)
*A61B 5/055* (2006.01)
*G06F 3/0488* (2013.01)
*G02B 27/01* (2006.01)
*G16H 20/30* (2018.01)

(52) U.S. Cl.
CPC ............ *G06F 3/015* (2013.01); *G09B 5/02* (2013.01); *G16H 20/30* (2018.01); *A61B 5/055* (2013.01); *A61B 2505/09* (2013.01); *G02B 2027/0141* (2013.01); *G06F 3/0488* (2013.01); *G06F 2203/011* (2013.01)

(56) References Cited

U.S. PATENT DOCUMENTS

| | | | | |
|---|---|---|---|---|
| 8,554,325 | B2* | 10/2013 | Molnar | A61B 5/04014 607/45 |
| 8,706,241 | B2* | 4/2014 | Firlik | A61B 5/16 607/48 |
| 8,886,323 | B2* | 11/2014 | Wu | A61N 1/36171 607/45 |
| 9,314,190 | B1* | 4/2016 | Giuffrida | A61B 5/11 |
| 2005/0171577 | A1* | 8/2005 | Cohen | A61N 1/36003 607/48 |
| 2007/0016265 | A1* | 1/2007 | Davoodi | G16H 50/50 607/48 |
| 2008/0312549 | A1* | 12/2008 | Levin | A61B 5/0488 600/546 |
| 2013/0338539 | A1* | 12/2013 | Bailey | A61B 5/1101 600/595 |
| 2013/0339908 | A1* | 12/2013 | Bailey | G06F 3/017 715/863 |
| 2014/0277582 | A1* | 9/2014 | Leuthardt | A61F 2/54 623/25 |
| 2014/0336722 | A1* | 11/2014 | Rocon De Lima | A61N 1/36025 607/45 |
| 2014/0347392 | A1* | 11/2014 | Odessky | G06T 13/40 345/633 |
| 2014/0371599 | A1* | 12/2014 | Wu | A61B 5/0077 600/476 |
| 2014/0379046 | A1* | 12/2014 | Tcheng | A61N 1/36067 607/48 |
| 2015/0321010 | A1* | 11/2015 | Marnfeldt | A61N 1/36067 607/45 |
| 2016/0015994 | A1* | 1/2016 | Cabrerizo | A61N 2/006 600/14 |
| 2017/0046971 | A1* | 2/2017 | Moreno | G09B 19/00 |
| 2017/0136295 | A1* | 5/2017 | Tholkes | A63B 22/0664 |
| 2017/0156663 | A1* | 6/2017 | Heruth | A61B 5/0488 |
| 2017/0258390 | A1* | 9/2017 | Howard | A61B 5/16 |
| 2017/0312579 | A1* | 11/2017 | Nakashima | A61H 1/0244 |
| 2018/0296424 | A1* | 10/2018 | Parra | A61F 2/50 |

FOREIGN PATENT DOCUMENTS

| | | | |
|---|---|---|---|
| WO | WO-2016-002207 | A1 | 1/2016 |
| WO | WO-2016002207 | A1 * | 1/2016 ............ A61H 1/02 |

OTHER PUBLICATIONS

Rocon; "Multimodal BCI-Mediated FES Suppression of Pathological Tremor"; 2010; https://ieeexplore.ieee.org/stamp/stamp.jsp?tp=&arnumber=5627914 (Year: 2010).*

Reaz; "Techniques of EMG signal analysis: detection, processing, classification and applications"; 2006; https://www.ncbi.nlm.nih.gov/pmc/articles/PMC1455479/ (Year: 2006).*

Davies; Near-Infrared Spectroscopy in the Monitoring of Adult Traumatic Brain Injury:A Review; 2015; https://www.ncbi.nlm.nih.gov/pmc/articles/PMC4492772/ (Year: 2015).*

Hoshi; "Functional near-infrared optical imaging: Utility and limitations in human brain mapping"; 2003; https://onlinelibrary.wiley.com/doi/abs/10.1111/1469-8986.00053 (Year: 2003).*

* cited by examiner

REHABILITATION SYSTEM

BACKGROUND

1. Technical Field

The present invention relates to a rehabilitation system.

2. Related Art

According to the related art, a rehabilitation system which decides the amount of training based on the result of analysis of brain waves before the start of rehabilitation training is known, for example, as disclosed in WO2016/002207. This can provide a rehabilitation program suitable for the patient, and improved effects of the rehabilitation can be expected.

However, the rehabilitation system disclosed in WO2016/002207 has a problem that it is difficult to cope with changes in the condition of the patient during training. For example, if the condition of the patient deteriorates during training, it may be difficult to continue training. Meanwhile, if the condition of the patient becomes better during training, the patient can accept training with higher load. With the rehabilitation system disclosed in WO2016/002207, it is difficult to cope with changes in the condition of the patient when such changes take place during training.

SUMMARY

An advantage of some aspects of the invention is to solve at least a part of the problems described above, and the invention can be implemented as the following configurations or application examples.

APPLICATION EXAMPLE 1

A rehabilitation system according to this application example includes: a brain activity measuring device which measures brain activity of a patient who carries out training based on a set amount of training; a motion measuring device which measures a motion state of a paralyzed site of the patient; a spasticity state determiner which determines a spasticity state based on the brain activity and the motion state; an updater which updates the amount of training based on a result of determination by the spasticity state determiner; and a presentation device which presents the updated amount of training to the patient.

According to this application example, the spasticity state is determined based on the result of measuring the brain activity and the motion state, and the amount of training can be updated based on the determined spasticity state. The updated amount of training can be presented to the patient during training. With this rehabilitation system, the amount of training updated in response to changes in the condition of the patient during training can be presented to the patient. Therefore, it is possible to cope with changes in the condition of the patient during training.

APPLICATION EXAMPLE 2

In the rehabilitation system according to the application example, it is preferable that the updater updates the amount of training in such a way as to reduce the amount of training when the result of determination by the spasticity state determiner indicates a spasticity.

According to this application example, the amount of training which overloads the patient having a spasticity can be reduced.

APPLICATION EXAMPLE 3

In the rehabilitation system according to the application example, it is preferable that the spasticity state determiner detects a motion intention from a result of measuring the brain activity, detects muscle activity from a result of measuring the motion state, and determines the spasticity state based on a result of detection of the motion intention and a result of detection of the muscle activity.

According to this application example, the spasticity state can be determined based on the motion intention detected from the result of measuring the brain activity and the muscle activity detected from the result of measuring the motion state.

APPLICATION EXAMPLE 4

In the rehabilitation system according to the application example, it is preferable that the spasticity state determiner determines that it is the spasticity, when the motion intention is not detected from the result of measuring the brain activity and the muscle activity is detected from the result of measuring the motion state.

According to this application example, it can be determined as a spasticity when the motion intention is not detected and the muscle activity is detected.

APPLICATION EXAMPLE 5

In the rehabilitation system according to the application example, it is preferable that the spasticity state determiner determines that a motion intention is detected when the result of measuring the brain activity exceeds a predetermined threshold.

According to this application example, it can be detected that a motion intention is detected, based on that the result of measuring the brain activity exceeds the predetermined threshold.

APPLICATION EXAMPLE 6

In the rehabilitation system according to the application example, it is preferable that the spasticity state determiner determines that muscle activity is detected when the result of measuring the motion state exceeds a predetermined threshold.

According to this application example, it can be determined that muscle activity is detected, based on that the result of measuring the motion state exceeds the predetermined threshold.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, embodiments of the invention will be described with reference to the drawings. In the illustrations below, individual members are not to scale in order to show these members in recognizable sizes.

Embodiment 1

Figure 1:
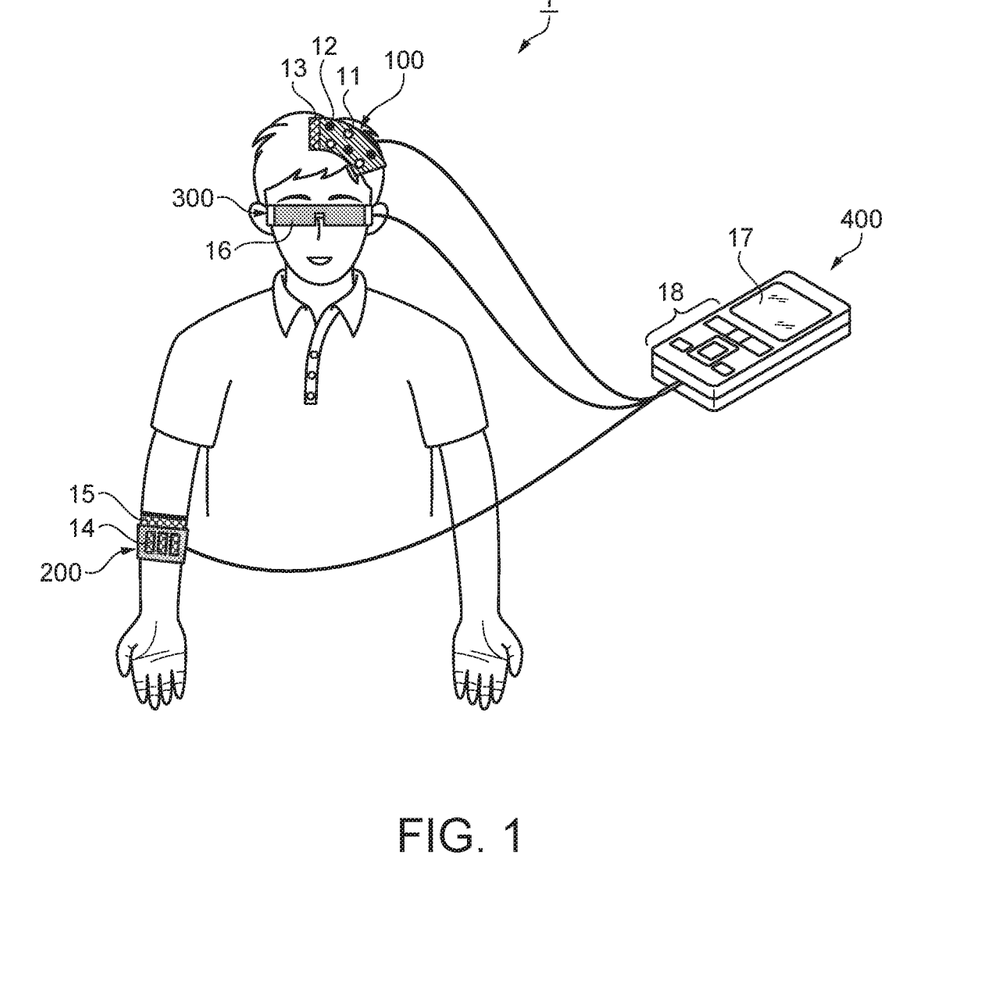
FIG. 1 is a schematic view showing the configuration of a rehabilitation system according to Embodiment 1.

FIG. 1 is a schematic view showing the configuration of a rehabilitation system 1 according to Embodiment 1. The rehabilitation system 1 includes a brain activity measuring device 100, a motion measuring device 200, a presentation device 300, and a control device 400. As illustrated, the rehabilitation system 1 is a system for supporting rehabilitation of a patient with a paralyzed site. In the description below, the term "rehabilitation" may be abbreviated as "rehab".

First, the schematic configurations of the brain activity measuring device 100, the motion measuring device 200, the presentation device 300, and the control device 400 according to Embodiment 1 will be described. The brain activity measuring device 100 is installed on the head of a patient and measures the brain activity of the patient. The motion measuring device 200 is stalled at a paralyzed site of the patient and measures the motion state of the patient. The control device 400 receives the results of measurement by the brain activity measuring device 100 and the motion measuring device 200, determines a motion intention and muscle activity, and makes a determination on the spasticity state according to the result of determining the motion intention and muscle activity. The control device 400 updates the amount of training for rehabilitation, based on the result of the determination on the spasticity state. The control device 400 transmits the updated amount of training to the presentation device 300, which presents the amount of training to the patient.

In this embodiment, the brain activity measuring device 100 is a near-infrared spectroscopy (NIRS) device which acquires the hemoglobin concentration in the cerebral blood flow and includes a light source 11, a light receiver 12, and a cerebral blood flow detection circuit 13.

The light source 11 and the light receiver 12 are installed in contact with the scalp of the patient. In this embodiment, the brain activity measuring device 100 includes a plurality of light sources 11 and a plurality of light receivers 12. The light outputted from each light source 11 is absorbed by the cerebral blood flow. Each light receiver 12 acquires the light intensity after the absorption, on the scalp surface. The cerebral blood flow detection circuit 13 calculates the absorbance from the acquired light intensity and the light intensity of the light source. The absorbance of hemoglobin in the cerebral blood flow is decided by the wavelength of the light. Therefore, the cerebral blood flow detection circuit 13 processes variations in the calculated absorbance and thus calculates the amount of change in the hemoglobin concentration in the brain region situated between the light source 11 and the light receiver 12. The brain activity measuring device 100 measures the brain activity of the patient, based on the calculated amount of change in the hemoglobin concentration. That is, in this embodiment, the brain activity measuring device 100 measures the brain activity, based on the hemoglobin concentration in the cerebral blood flow. The brain activity measuring device 100 transmits the result of measuring the brain activity to the control device 400 as a result of brain activity measurement. The cerebral blood flow detection circuit 13 has a transmission function. The result of brain activity measurement is transmitted to the control device 400 via wired communication by the transmission function of the cerebral blood flow detection circuit 13. The transmission measure may be wired or wireless.

In this embodiment, the motion measuring device 200 is a device (electromyography or EMG) which acquires surface potential and includes an electrode 14 and an electromyography detection circuit 15.

The electrode 14 is installed on the skin of the paralyzed site of the patient. In this embodiment, the motion measuring device 200 includes a plurality of electrodes 14. When the patient moves muscles of the paralyzed site, motor neurons of neural cells present in the muscles become active. In response to the activity of the motor neurons, the electrode 14 acquires surface potential on the skin situated in the muscle region where the motor neurons are active. The electromyography detection circuit 15 processes variations in the acquired surface potential and thus calculates the amount of change in the surface potential at the electrode 14. The motion measuring device 200 measures the motion state of the paralyzed site of the patient, based on the amount of change in the surface potential detected via the electrode 14. That is, in this embodiment, the motion measuring device 200 measures the motion state, based on the surface potential of the paralyzed site of the patient. The motion measuring device 200 transmits the result of measuring the motion state to the control device 400 as a result of motion state measurement. The electromyography detection circuit 15 has a transmission function. The result of motion state measurement is transmitted to the control device 400 via wired communication by the transmission function of the electromyography detection circuit 15. The transmission measure may be wired or wireless.

The presentation device 300 is a head-mounted display device (HMD). The control device 400 is an HMD controller. The presentation device 300 includes a display 16. The control device 400 includes a touch pad 17 and an operation button set 18.

The display 16 can allow the patient to visually recognize a virtual image. The display 16 is an optical see-through display which enables direct visual recognition of the real space. The presentation device 300 can present the amount of training to the patient via the display 16. The touch pad 17 detects a contact operation on the operation surface of the touch pad 17 and outputs a signal corresponding to the detection content. As the touch pad 17, various touch pads such as electrostatic, pressure detection-type, and optical touch pads can be employed. The operation button set 18 includes various operation buttons. The operation button set 18 detects an operation on each operation button and outputs a signal corresponding to the detection content. The touch pad 17 and the operation button set 18 are operated by the user. The user may be not only the patient but also an attendant such as a doctor or physiotherapist.

Figure 2:
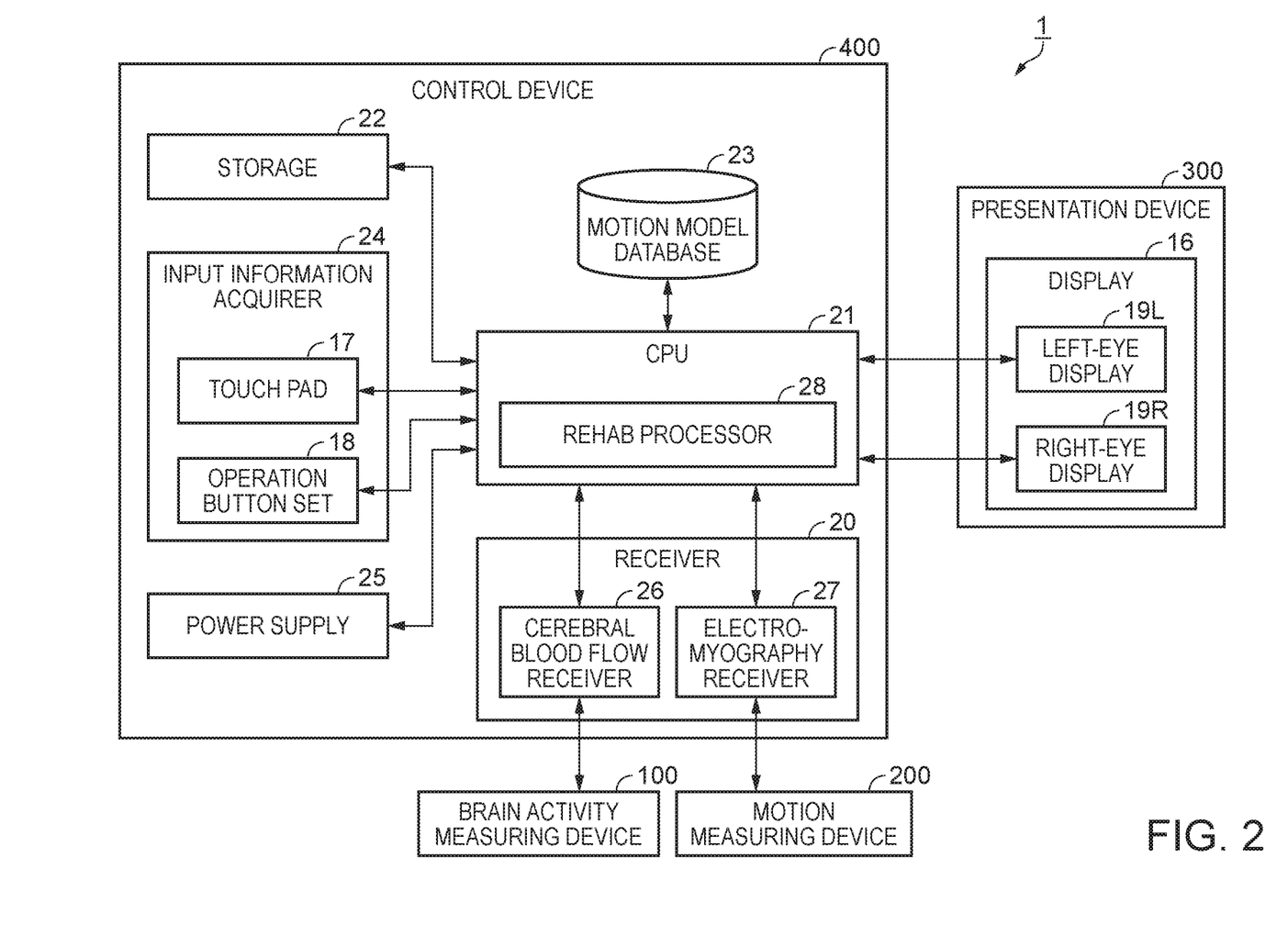
FIG. 2 is a block diagram showing the configuration of the rehabilitation system.

FIG. 2 is a block diagram functionally showing the configurations of the presentation device 300 and the control device 400.

The presentation device 300 has a left-eye display 19L and a right-eye display 19R and is connected to a CPU 21 of the control device 400.

The right-eye display 19R has a configuration symmetrical to the configuration of the left-eye display 19L and displays an image similar to the image displayed on the left-eye display 19L. As a result, the patient can recognize the images by wearing the presentation device 300 on the head. Also, since at least a part of the light from the real space is transmitted through the presentation device 300, the patient with the presentation device 300 left on the head can see the real space.

The control device 400 includes a receiver 20, a CPU (central processing unit) 21, a storage 22, a motion model database 23, an input information acquirer 24, and a power supply 25.

The receiver 20 includes a cerebral blood flow receiver 26 and an electromyography receiver 27. The cerebral blood flow receiver 26 receives the result of brain activity measurement transmitted from the brain activity measuring device 100. The electromyography receiver 27 receives the result of motion state measurement transmitted from the motion measuring device 200. The receiver 20 outputs the result of brain activity measurement received by the cerebral blood flow receiver 26 and the result of motion state measurement received by the electromyography receiver 27 to the CPU 21.

The CPU 21 includes a rehab processor 28. The CPU 21 reads out a computer program stored in the storage 22 and executes the program, thus realizing various functions. Specifically, when a detection content of an operation is inputted from the input information acquirer 24, the CPU 21 realizes the function of executing processing corresponding to the detection content, the function of reading data from and writing data to the storage 22, and the function of controlling the supply of electricity to each component from the power supply 25. The rehab processor 28 carries out the setting of the amount of training and the update of the amount of training, based on inputs from the cerebral blood flow receiver 26 and the electromyography receiver 27.

The CPU 21 also reads out a rehab program stored in the storage 22 and executes the rehab program, thus functioning as the rehab processor 28 executing rehab processing for the recovery of functions of a disabled body part. In this embodiment, the rehab processing is for the recovery of functions of a hand as a disabled body part. The disability may be, for example, paralysis due to cerebral apoplexy.

The storage 22 is made up of a ROM (read only memory), RAM (random access read only memory), DRAM (dynamic random access memory), HDD (hard disk drive) or the like. In the storage 22, various computer programs including an OS (operating system) are stored. In this embodiment, one of the stored computer programs is the rehab program.

The motion model database 23 is a database in which motion models are accumulated. A motion model is dynamic image data which models a target motion in rehab. The motion model may be a set of still image data instead of dynamic image data. Moreover, the motion model may be data made up of a set of feature point positions on the hand and can be replaced with any data that can construct a dynamic image. Also, the motion model may include a parameter such as the number of times and speed of the motion.

The input information acquirer 24 includes the touch pad 17 and the operation button set 18 which are described above. The input information acquirer 24 inputs a signal corresponding to the detection content from the touch pad 17 or the operation button set 18.

The power supply 25 supplies electricity to each component that needs electricity, provided in the control device 400 and the presentation device 300.

Figure 3:
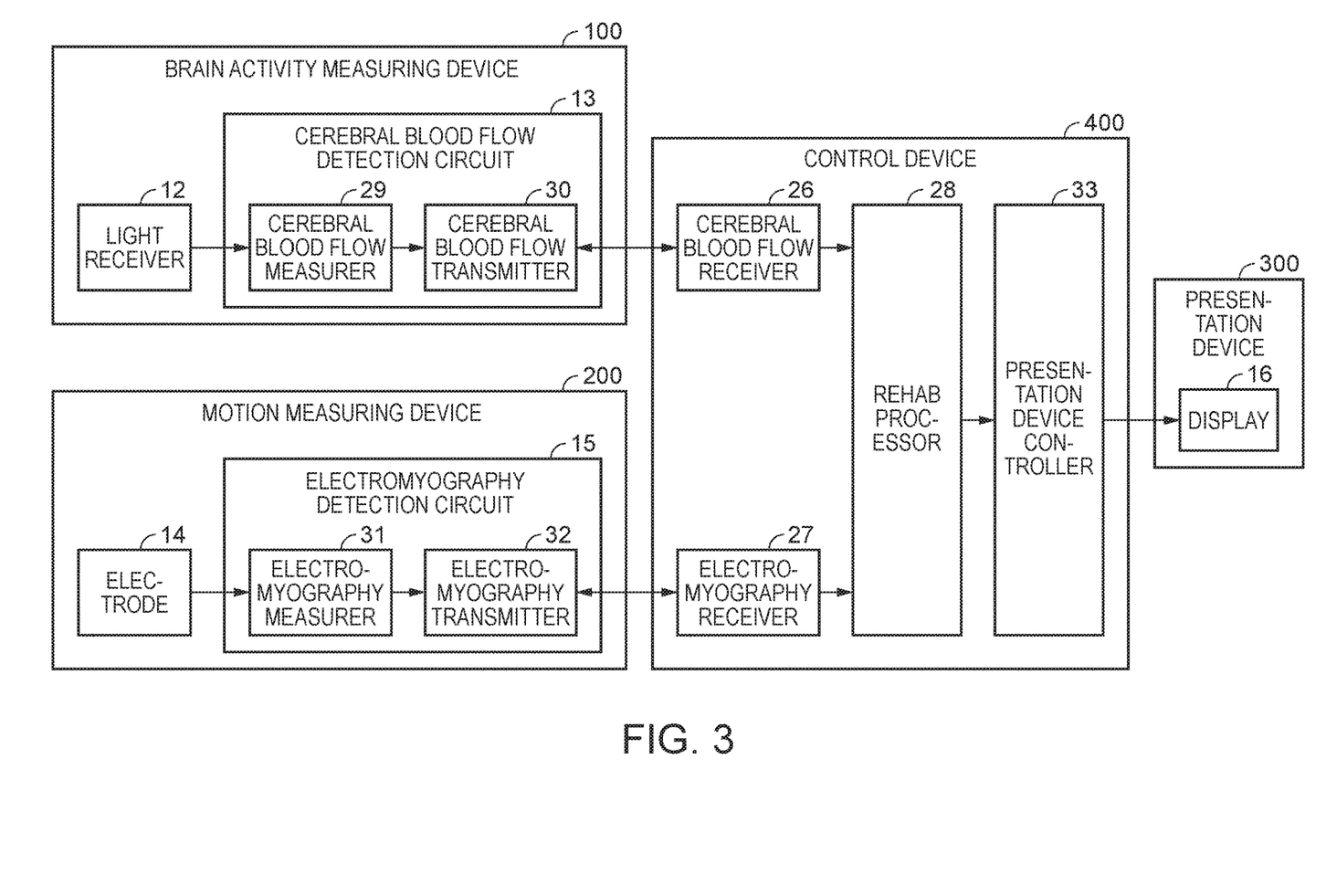
FIG. 3 is a control block diagram of the rehabilitation system.

FIG. 3 is a control block diagram of the rehabilitation system 1.

As described above, the brain activity measuring device 100 has the light receiver 12 and the cerebral blood flow detection circuit 13. The cerebral blood flow detection circuit 13 has a cerebral blood flow measurer 29 and a cerebral blood flow transmitter 30. An output signal from the light receiver 12 is subjected to signal processing by the cerebral blood flow measurer 29 and then transmitted from the cerebral blood flow transmitter 30 to the control device 400.

The motion measuring device 200 has the electrode 14 and the electromyography detection circuit 15. The electromyography detection circuit 15 has an electromyography measurer 31 and an electromyography transmitter 32. An output signal from the electrode 14 is subjected to signal processing by the electromyography measurer 31 and then transmitted from the electromyography transmitter 32 to the control device 400.

The control device 400 has the cerebral blood flow receiver 26, the electromyography receiver 27, the rehab processor 28, and a presentation device controller 33. The cerebral blood flow receiver 26 receives the result of brain activity measurement transmitted from the brain activity measuring device 100. The electromyography receiver 27 receives the result of motion state measurement transmitted from the motion measuring device 200. The rehab processor 28, described later, outputs the amount of training to be presented to the patient, to the presentation device controller 33, based on the result of brain activity measurement and the result of motion state measurement. The presentation device controller 33 prepares a display image based on the amount of training inputted from the rehab processor 28.

The presentation device 300 has the display 16. The display 16 presents the amount of training to the patient, based on an instruction from the control device 400.

Figure 4:
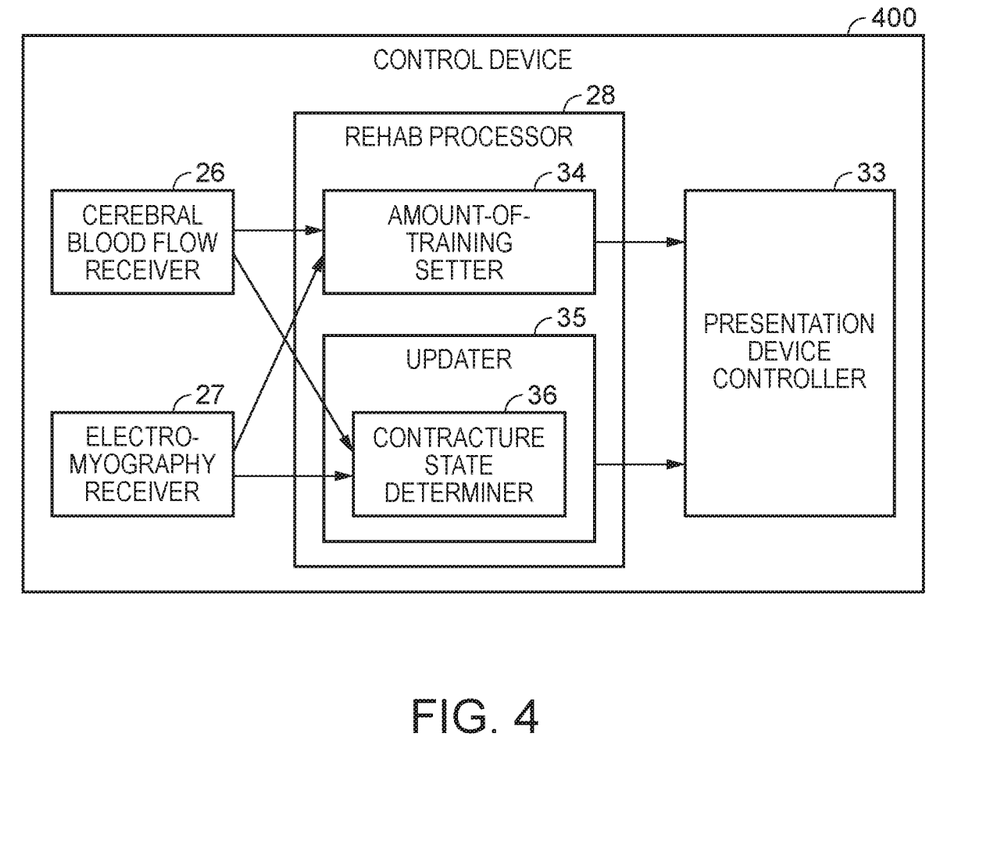
FIG. 4 is a control block diagram of a control device.

FIG. 4 is a control block diagram of the control device 400.

As shown in FIG. 4, the rehab processor 28 has an amount-of-training setter 34 and an updater 35. The updater 35 has a spasticity state determiner 36.

The amount-of-training setter 34 sets the amount of training, based on the result of brain activity measurement inputted from the cerebral blood flow receiver 26 and the result of muscle activity measurement inputted from the electromyography receiver 27. In this embodiment, for example, the initial amount of training is set, based on the result of brain activity measurement on the initial stage (hereinafter referred to as the result of initial brain activity measurement) and the result of motion state measurement on the initial stage (hereinafter referred to as the result of initial motion state measurement). The set amount of training is outputted to the presentation device controller 33.

The updater 35 updates the amount of training, based on the result of brain activity measurement inputted from the cerebral blood flow receiver 26 and the result of muscle activity measurement inputted from the electromyography receiver 27 during training. The spasticity state determiner 36 detects a motion intention, based on the result of brain activity measurement received by the cerebral blood flow receiver 26. The spasticity state determiner 36 also detects muscle activity, based on the result of motion state measurement received by the electromyography receiver 27. The spasticity state determiner 36 determines whether the patient is in a spasticity state or not, based on the result of the detection of a motion intention and the result of the detection of muscle activity. The updater 35 updates the amount of training for rehab, based on the result of the determination by the spasticity state determiner 36. The updated amount of training is outputted to the presentation device controller 33.

Figure 5:
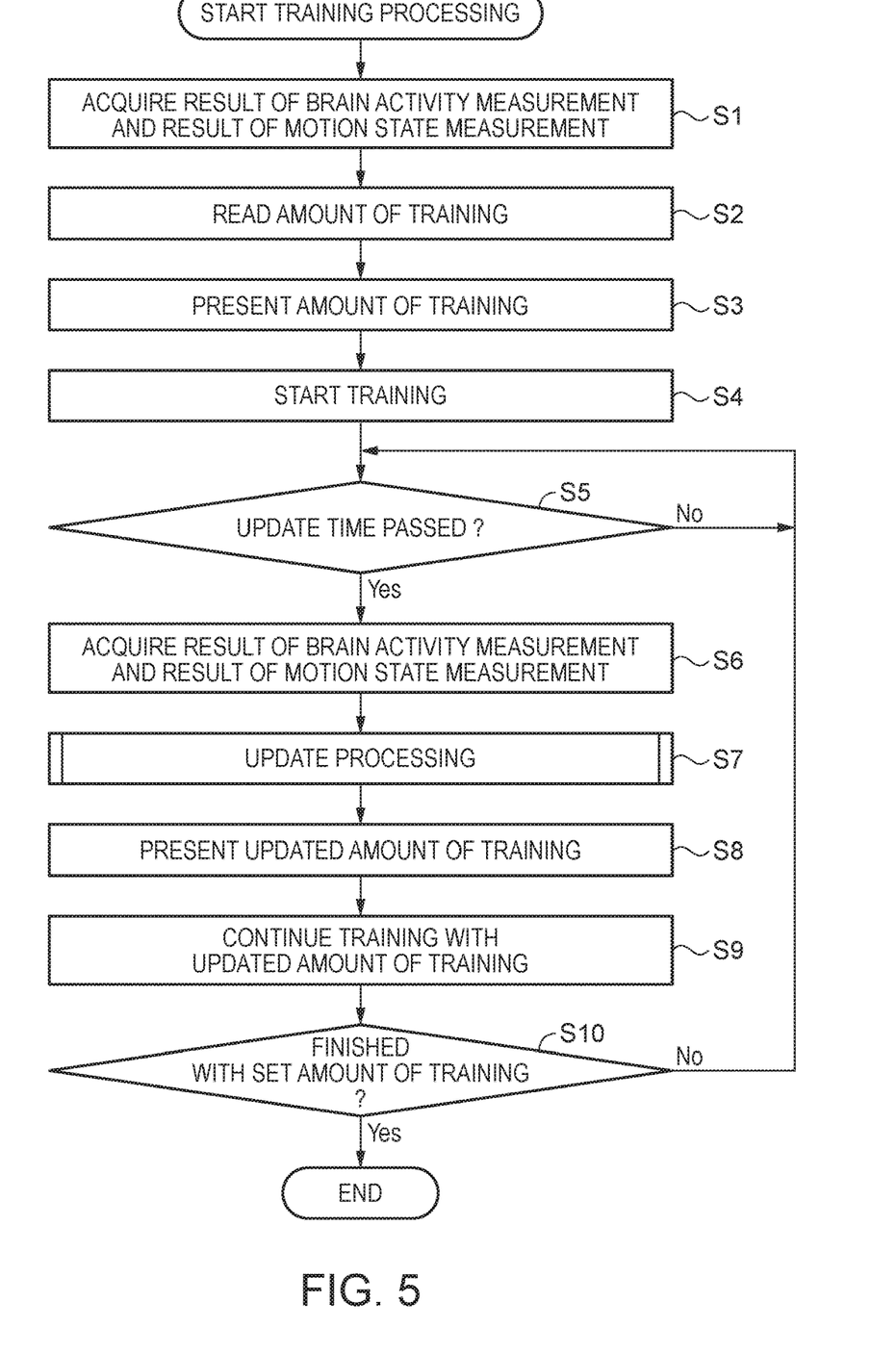
FIG. 5 is a flowchart showing training processing for rehabilitation with the rehabilitation system.

FIG. 5 is a flowchart showing training processing for rehabilitation with the rehabilitation system 1. This training processing is executed by the rehab processor 28 and is started by the CPU 21 when a predetermined operation using the touch pad 17 or the operation button set 18 of the input information acquirer 24 is accepted.

As the training processing is started, the CPU 21 in Step S1 acquires the result of brain activity measurement and the result of motion state measurement. In Step S1, the result of brain activity measurement and the result of motion state measurement when the patient is in a resting state are acquired. At this point, the brain activity measuring device 100 outputs the result of measuring the brain activity of the patient in the resting state to the control device 400 as the result of initial brain activity measurement, based on an instruction from the CPU 21. The motion measuring device 200 outputs the result of measuring the motion state of the patient in the resting state to the control device 400 as the result of initial motion state measurement, based on an instruction from the CPU 21. At this time, a display to instruct the patient to keep resting is presented on the presentation device 300. The term "initial" refers to a reference state for calculating the amount of change in the brain activity and the motion state, and in this embodiment, refers to the resting state where the patient is not moving. The result of initial brain activity measurement and the result of initial motion state measurement are saved in the storage 22 of the control device 400.

In Step S2, the CPU 21 reads the initially set amount of training from the storage 22. The amount of training is set according to the condition of the patient and includes a training intensity and a training content. The training content indicates the content of a motion in training that involves a motion from among different kinds of training for rehab.

The training content includes specifying of a site as a training target (hereinafter referred to as a training target site) and a movement to be made by the training target site. For example, in the case of a patient having a paralysis in the right forearm as an example, the right forearm is specified as the training target site. In this example, as the movement to be made by the training target site, the movement of closing and opening the right hand repeatedly is specified.

The training intensity is a parameter of training that involves a motion, and includes a motion speed, a motion time, a motion interval, and an update time. The motion speed indicates the speed of the movement to be made by the training target site. In the example where the right arm is specified as the training target site, the motion speed indicates the speed of closing and opening the hand. The motion time indicates the time for which the motion is carried out, and here indicates the time for which the movement of closing and opening the hand repeatedly is made. Instead of the motion time, the number of times of the motion may be used as a parameter. The number of times of the motion indicates the number of times the movement to be made repeatedly is repeated. The motion interval indicates the interval (time) between one movement and the next movement, of the movement to be made repeatedly. The update time indicates the time (interval) at which the amount of training is updated. The update of the amount of training will be described later.

As the initial setting of the amount of training, a paralyzed site and a plurality of amounts of training corresponding to the degrees of seriousness of the paralysis of the patient are saved in the storage 22. The initial setting is selected by the CPU 21 reading the content in the storage 22, based on an output from the input information acquirer 24. As a selection method, the initial setting may be selected by the patient or a physiotherapist, or may be selected based on the result of analysis of the brain activity of the patient. In the case of selecting the initial setting based on the result of analysis of the brain activity of the patient, for example, a method of deciding the amount of training according to the activity intensity in the alpha range (8 to 13 hertz) of the brain waves of the patient can be employed.

In Step S3, the CPU 21 causes the display 16 to display a display image based on the amount of training. This is carried out by the CPU 21 outputting an instruction to the presentation device controller 33. The presentation device 300 causes the display 16 to display the display image based on the amount of training in response to the instruction from the CPU 21. Thus, the amount of training is presented to the patient via the presentation device 300. The content to be presented may be a video showing the movement of the paralyzed site which the patient is to train, or may be an image showing the entire amount of training. As the video of the movement of the paralyzed site, for example, in the case of the example where the right arm is specified as the training target site, a video (dynamic image) of a hand closing and opening may be employed. The patient can make the movement of closing and opening the hand with this video. That is, the presentation of the amount of training can function as an instruction for training. Particularly in this embodiment, since a see-through HMD is employed as the presentation device 300, the patient can be allowed to visually recognize his/her own right art in such away as to overlap the video of the movement of closing and opening the hand. This can facilitate the enhancement of the effects of training through the video. As the presentation device 300, a non-see-through HMD may be employed as well. In this case, the patient cannot visually recognize any other scenes but the display content and therefore can concentrate on the video of the movement more easily.

In Step S4, the CPU 21 notifies the presentation device controller 33 of the start of training. This notification is carried out by the CPU 21 outputting an instruction of notification to the presentation device controller 33. The presentation device 300 causes the display 16 to display a display image showing a notification of the start of training, based on the instruction from the CPU 21. Thus, the patient starts training according to the display image displayed on the display 16. At this point, the CPU 21 saves the start time of training in the storage 22.

In Step S5, the CPU 21 determines whether the update time has passed. The passage of the update time is determined by determining whether the difference between the start time of training and the current time has reached the update time or not. If it is determined that the update time is reached (YES), the processing shifts to Step S6. If it is determined the update time is not reached (NO), the processing waits until the update time passes. The method for measuring the time elapsed is not limited to calculating the difference between the start time of training and the current time. Measuring the time from the start of training to the present with a timer can be employed as well.

In Step S6, the CPU 21 acquires the result of brain activity measurement and the result of motion state measurement during training. The brain activity measuring device 100 outputs the result of measuring the brain activity of the patient during training to the control device 400 as the result of brain activity measurement, based on an instruction from the CPU 21. The motion measuring device 200 outputs the result of measuring the motion state of the patient during training to the control device 400 as the result of motion state measurement, based on an instruction from the CPU 21.

In Step S7, the CPU 21 carries out update processing, described later, and then shifts to Step S8. In the update processing, the CPU 21 updates the amount of training, based on the result of brain activity measurement and the result of motion state measurement during training.

In Step S8, the CPU 21 causes the display 16 to display a display image, based on the amount of training (amount of training that is updated) outputted from the update processing, described later. This is carried out by the CPU 21 outputting an instruction to the presentation device controller 33. The presentation device 300 causes the display 16 to display the display image based on the amount of training that is updated (hereinafter referred to as the updated amount of training) in response to the instruction from the CPU 21. Thus, the updated amount of training is presented to the patient via the presentation device 300. The content to be presented may be a video showing the movement of the paralyzed site which the patient is to train, or may be an image showing the entirety of the updated amount of training.

In Step S9, the presentation device controller 33 issues a notification prompting the continuation of training based on the updated amount of training. This notification is carried out by the CPU 21 outputting an instruction of notification to the presentation device controller 33. The presentation device 300 causes the display 16 to display a display image showing a notification of the continuation of training in response to the instruction from the CPU 21. Thus, the patient continues training based on the updated amount of training according to the display image displayed on the display 16.

In Step S10, the CPU 21 determines whether training with the set amount of training is finished. This can be realized by determining whether the time elapsed from the start of training has reached the motion time or not. The CPU 21 calculates the difference between the start time of training and the current time and thus calculates the time elapsed. The CPU 21 then compares the time elapsed with the motion time that is set with the amount of training, and thus determines whether training with the set amount of training is finished or not. If it is determined that training with the set amount of training is finished (YES), the training processing ends. If it is determined that training with the set amount of training is not finished (NO), the processing returns to Step S5 to continue the training processing.

Figure 6:
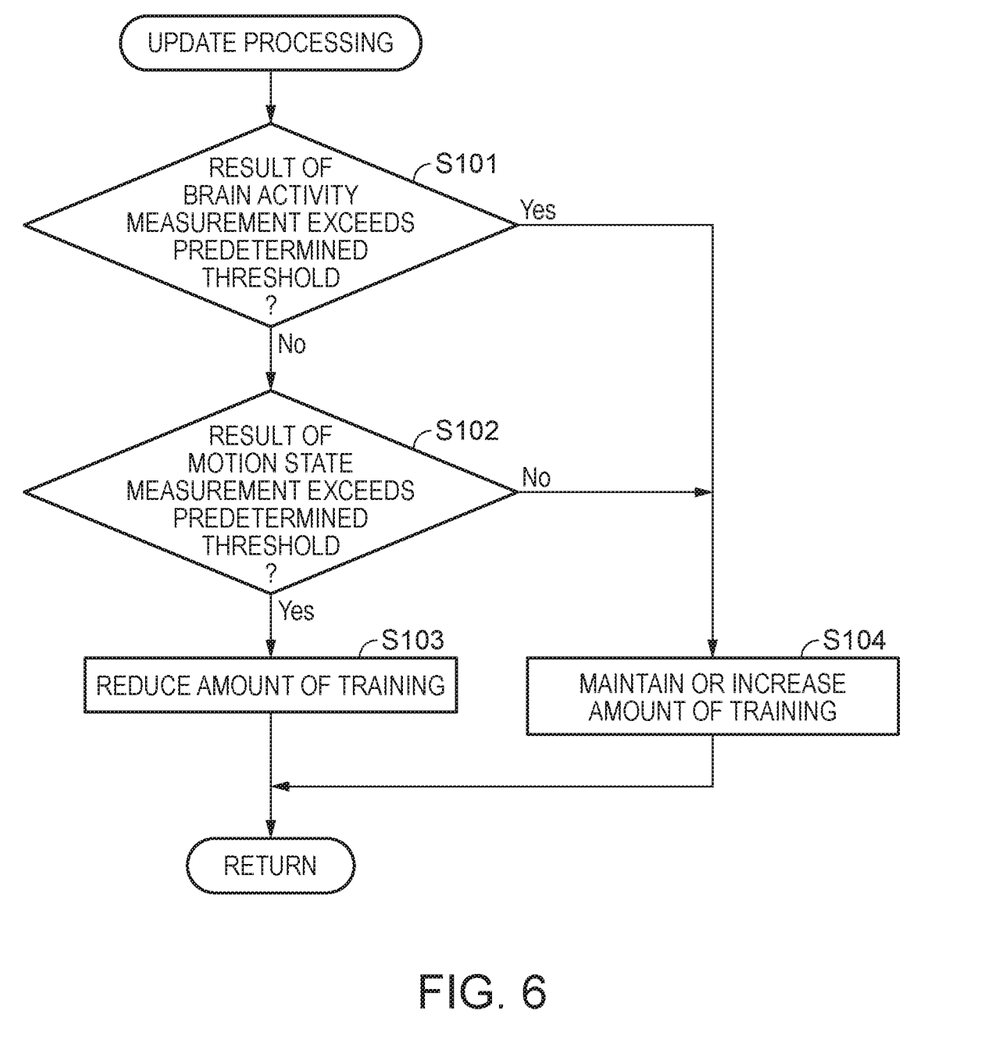
FIG. 6 is a flowchart showing update processing.

FIG. 6 is a flowchart of the update processing. This update processing is the processing of the updater 35 and is carried out by the CPU 21 every update time.

In the update processing, the CPU 21 updates the amount of training, based on the result of initial brain activity measurement and the result of brain activity measurement during training and also on the result of initial motion state measurement and the result of motion state measurement during training. As the update processing is started, the CPU 21 in Step S101 determines whether the result of brain activity measurement exceeds a predetermined threshold or not. The result of brain activity measurement during training is the result of brain activity measurement acquired in Step S6 in FIG. 5. At this point, if the result of brain activity measurement exceeds the predetermined threshold (YES), the CPU 21 determines that a motion intention is detected. The motion intention refers to brain activity generated when the training target site moves. In other words, the motion intension refers to brain activity generated when the patient moves intentionally. That is, the motion intention is an indicator indicating whether the motion is based on the intention of the patient or not. In this embodiment, the result of initial brain activity measurement is employed as the predetermined threshold. As the state where the predetermined threshold is exceeded, the state where the result of brain activity measurement during training is greater than the result of initial brain activity measurement and where there is a statistically significant difference between these is employed. As the state where there is a statistically significant difference, for example, the state where the p-value, which is a statistical value, is less than 0.05 can be employed. The CPU 21 compares the result of initial brain activity measurement saved in the storage 22 with the result of brain activity measurement during training. At this point, if the result of brain activity measurement during training is greater than the result of initial brain activity measurement (YES), it is determined that a motion intention is detected, and the processing shifts to Step S104. If a motion intention is not detected (NO), the processing shifts to Step S102.

In Step S102, the CPU 21 determines whether the result of motion state measurement exceeds a predetermined threshold or not. The result of motion state measurement during training is the result of motion state measurement acquired in Step S6 in FIG. 5. At this point, if the result of motion state measurement exceeds the predetermined threshold (YES), the CPU 21 determines that muscle activity is detected. The muscle activity refers to the movement of muscles generated when the training target site moves. In this embodiment, the result of initial motion state measurement is employed as the predetermined threshold. As the state where the predetermined threshold is exceeded, the state where the result of motion state measurement during training is greater than the result of initial motion state measurement and where there is a statistically significant difference between these is employed. As the state where there is a statistically significant difference, for example, the state where the p-value, which is a statistical value, is less than 0.05 can be employed. The CPU 21 compares the result of initial motion state measurement saved in the storage 22 with the result of motion state measurement during training. At this point, if the result of motion state measurement during training is greater than the result of initial motion state measurement (YES), it is determined that muscle activity is detected, and the processing shifts to Step S103. If muscle activity is not detected (NO), the processing shifts to Step S104. The processing of Step S101 and the processing of Step S102 correspond to the processing of the spasticity state determiner 36.

In Step S103, the CPU 21 reduces the amount of training and then the processing returns to Step S8 of the training processing (FIG. 5). When the processing shifts to Step S103, it is determined that the patient is in the spasticity state. The spasticity state refers to the state where muscle activity is generated without any motion intention of the patient. If the patient during training has a spasticity, it is conceivable that the amount of training is overloading the patient. Thus, in Step S103, the CPU 21 reduces the amount of training. The reduction in the amount of training is realized by the CPU 21 selecting an amount of training from data of a plurality of reduced amounts of training saved in advance in the storage 22. The reduction in the amount of training may be, for example, reducing the motion speed, making the motion easier, or the like. In this embodiment, for example, slowing down the speed of the training movement, employing a movement of stretching the paralyzed hand with the normal hand as the training movement, or the like, may be employed.

In Step S104, the CPU 21 maintains the amount of training or increase the amount of training and then the processing returns to Step S8 of the training processing (FIG. 5). The increase in the amount of training is realized by the CPU 21 selecting an amount of training from data of a plurality of increased amounts of training saved in advance in the storage 22. The increase in the amount of training may be, for example, increasing the motion speed, making the motion more difficult, or the like. In this embodiment, for example, increasing the speed of the training motion, employing a movement of bending and stretching each finger as the training movement, or the like, may be employed.

As described above, the rehabilitation system 1 according this embodiment can achieve the following effects.

The rehabilitation system 1 can cope with changes in the condition of the patient during training. In the rehabilitation system 1, the spasticity state is determined based on the results of measuring the brain activity and the motion state, and the amount of training can be updated based on the determined spasticity state. The updated amount of training can be presented to the patient during training. With the rehabilitation system 1, the amount of training updated according to changes in the condition of the patient during training can be presented to the patient. Therefore, it is possible to cope with changes in the condition of the patient during training. For example, when the condition of the patient deteriorates during training, the patient can continue training based on the reduced updated amount of training. Meanwhile, when the condition of the patient gets better during training, the patient can continue training based on the updated amount of training which is an amount of training with higher load.

In this embodiment, as the CPU 21 executes a program, each functional component in the control device 400 is realized by the operation of software. However, each functional component in the control device 400 can also be realized, for example, by hardware such as an integrated circuit or by the collaboration of software and hardware.

Embodiment 2

Figure 7:
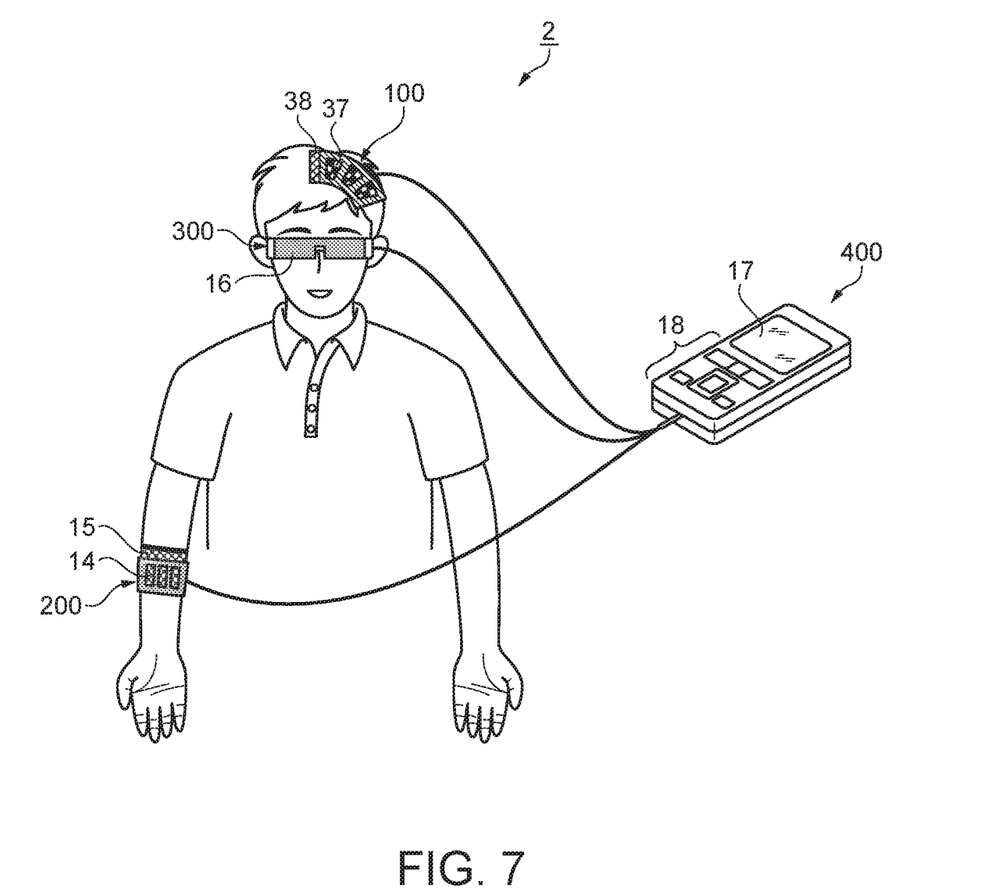
FIG. 7 is a schematic view showing the configuration of a rehabilitation system according to Embodiment 2.

FIG. 7 is a schematic view showing the configuration of a rehabilitation system 2 according to Embodiment 2. The rehabilitation system 2 according to this embodiment will be described with reference to FIG. 7. The same components as in Embodiment 1 are denoted by the same reference numbers and will not be described further.

In FIG. 7, a brain activity measuring device 100 according to Embodiment 2 is an electroencephalograph (EEG) which acquires cranial nerve potential, and includes a brain wave electrode 37 and a brain wave measuring circuit 38.

The brain wave electrode 37 is installed in contact with the scalp of the patient. In this embodiment, the brain activity measuring device 100 includes a plurality of brain wave electrodes 37. When the patient intends to move, brain neurons work. The brain wave electrode 37 acquires the surface potential on the skin situated in an active brain region in response to the activity of brain neurons. A part of the plurality of brain wave electrodes 37 may be set as a reference electrode, and a reference surface potential at the time of detecting a motion intention may be acquired at the reference electrode. The brain wave measuring circuit 38 processes variations in the acquired surface potential and thus calculates the amount of change in the surface potential detected via the brain wave electrodes 37. The brain activity measuring device 100 measures the brain activity of the patient, based on the amount of change in the surface potential detected via the brain wave electrodes 37. That is, in this embodiment, the brain activity measuring device 100 measures the brain activity based on the surface potential of the scalp of the patient. The brain activity measuring device 100 transmits the result of measuring the brain activity to the control device 400 as a result of brain activity measurement. The brain wave measuring circuit 38 has a transmission function. The result of brain activity measurement is transmitted to the control device 400 via wired communication by the transmission function of the brain wave measuring circuit 38. The transmission measure may be wired or wireless.

In Embodiment 2, in Step S101 shown in FIG. 6, the result of measurement by the reference electrode of the brain wave electrodes 37 may be used as the predetermined threshold. The CPU 21 compares the result of measurement by the reference electrode with the result of brain activity measurement by the electrodes other than the reference electrode, of the brain wave electrodes 37. If the result of brain activity measurement by the other electrodes is greater than the result of measurement by the reference electrode, it is determined that a motion intention is detected and the processing of Step S104 is carried out. If a motion intention is not detected, the processing of Step S102 is carried out.

Embodiment 2 has effects similar to those of Embodiment 1. Also, as described above, the rehabilitation system 2 according to this embodiment can achieve the following effects in addition to the effects of Embodiment 1.

The rehabilitation system can be applied to the case when the cerebral blood flow of a patient is difficult to measure. For example, with a patient who has experienced cerebral apoplexy, it may be difficult to stably acquire a cerebral blood flow because of damage to blood vessels or swelling of a brain site. Brain waves are acquired by measuring the surface potential of neural cells and therefore can be easily measured with a patient who has experienced cerebral apoplexy.

The invention is not limited to the foregoing embodiments. Various changes and improvements can be added to the embodiments. Modifications will be described below.

Modification 1

In Embodiment 1, a NIRS device which measures the cerebral blood flow is used as the brain activity measuring device 100. As a modification to this, an fMRI (functional magnetic resonance imaging) device may be used as the brain activity measuring device 100. The fMRI device is a device which measures the magnetic susceptibility of hemoglobin in the cerebral blood flow via a magnetic field. The brain activity of the patient is measured, based on the amount of change in the magnetic susceptibility of hemoglobin.

Modification 2

In Embodiment 2, an EEG which measures the surface potential of cranial nerves is used as the brain activity measuring device 100. As a modification to this, an MEG (magnetoencephalograph) may be used as the brain activity measuring device 100. The MEG is a device which measures a magnetic field based on the surface potential on the scalp, generated by the activity of brain neurons. The brain activity of the patient is measured, based on the magnetic field generated by the brain activity.

Modification 3

In the foregoing embodiments and modifications, an electromyograph which measures the surface potential of muscles is used as the motion measuring device 200. As a modification to this, MMG (mechanomyogram) may be used. The MMG measures movements of muscles as vibrations on the skin surface. Also, a joint movement angle may be used. As this joint movement angle, the joint movement angle at a paralyzed site is measured by an acceleration sensor or goniometer.

Modification 4

In the foregoing embodiments and modifications, the HMD is a see-through display device which does not shut off the field of view of the user when the user wears the HMD. As a modification to this, the HMD may be a non-see-through display device which shuts off the field of view of the user. Also, while the HMD is described as having the left-eye display 19L and the right-eye display 19R, the HMD may instead have a display for one eye only. Moreover, not only the HMD but also a liquid crystal display or projector may used for display.

Modification 5

In the foregoing embodiments and modifications, examples where functions of a hand are to be recovered with the rehabilitation system 1 or the rehabilitation system 2 are described. As a modification of the rehabilitation system 1 or the rehabilitation system 2, a rehabilitation system for recovering functions of a wrist or arm joint may be employed. Also, a rehabilitation system for recovering functions of a toe, ankle or knee may be employed.

Modification 6

In the foregoing embodiments and modifications, the control device 400 is an HMD controller. As a modification to this, the control device 400 may be integrated with a device such as the presentation device 300, the brain activity measuring device 100, or the motion measuring device 200.

The entire disclosure of Japanese Patent Application No. 2016-204929 filed Oct. 19, 2016 is expressly incorporated by reference herein.

What is claimed is:

1. A rehabilitation system comprising:
   a spectroscopy device that is attachable onto a scalp of a patient, the spectroscopy device having a light source, a light receiver, and a brain activity detection circuit, the light source emitting light toward a blood flow under the scalp, the light receiver obtaining an intensity of reflected light that is generated by reflecting the light off the blood flow, the brain activity detection circuit configured to detect brain activity of the patient who carries out a set amount of training based on the obtained intensity;
   an electromyography device having an electrode and a motion detection circuit connected to the electrode, the electrode abutting a paralyzed part of the patient to detect a movement of muscles of the paralyzed part of the patient, the motion detection circuit being configured to detect a surface potential change acquired by the electrode so as to measure a motion state of the paralyzed part of the patient;
   a head-mounted display configured to display a motion image, the head-mounted display having an optically see-through display so that the paralyzed part, which is overlapped with the motion image, is observed by the patient through the head-mounted display, the motion image having first and second images;
   a memory configured to store a computer program, an initial brain activity of the patient, an initial motion state of the patient, and an initial amount of training; and
   a processor configured to execute the computer program so as to:
      obtain the initial brain activity of the patient, the initial motion state of the patient, and the initial amount of training from the memory;
      set the initial amount of training as the set amount of training;
      display the first image on the head-mounted display, the first image corresponding to the initial amount of training of the paralyzed part so as to encourage the patient to move the paralyzed part according to the first image;
      obtain a first brain activity of the patient via the spectroscopy device and a first motion state of the patient via the electromyography device while the initial amount of training is set as the set amount of training and the patient moves the paralyzed part according to the first image;
      determine a spasticity state of the paralyzed part of the patient when the first brain activity is equal to or less than the initial brain activity and the first motion state is more than the initial motion state;
      reduce the set amount of training to a first amount of training when the processor determines the spasticity state of the paralyzed part of the patient;
      display the second image on the head-mounted display when the processor determines the spasticity state of the paralyzed part of the patient, the second image corresponding to the first amount of training of the paralyzed part so as to encourage the patient to move the paralyzed part according to the second image, a motion speed of the second image being slower than a motion speed of the first image; and
      stop the training when the processor determines that the set amount of training is finished by the patient.

2. A rehabilitation system comprising:
   a spectroscopy device that is attachable onto a scalp of a patient, the spectroscopy device having a light source, a light receiver, and a brain activity detection circuit, the light source emitting light toward a blood flow under the scalp, the light receiver obtaining an intensity of reflected light that is generated by reflecting the light off the blood flow, the brain activity detection circuit configured to detect brain activity of the patient who carries out a set amount of training based on the obtained intensity;
   an electromyography device having an electrode and a motion detection circuit connected to the electrode, the electrode abutting a paralyzed part of the patient to detect a movement of muscles of the paralyzed part of the patient, the motion detection circuit being configured to detect a surface potential change acquired by the electrode so as to measure a motion state of the paralyzed part of the patient;
   a head-mounted display configured to display a motion image, the head-mounted display having an optically see-through display so that the paralyzed part, which is overlapped with the motion image, is observed by the patient through the head-mounted display, the motion image having first, second, and third images;

a memory configured to store a computer program, an initial brain activity of the patient, an initial motion state of the patient, and an initial amount of training; and a processor configured to execute the computer program so as to:
- obtain the initial brain activity of the patient, the initial motion state of the patient, and the initial amount of training from the memory;
- set the initial amount of training as the set amount of training;
- display the first image on the head-mounted display, the first image corresponding to the initial amount of training of the paralyzed part so as to encourage the patient to move the paralyzed part according to the first image;
- obtain a first brain activity of the patient via the spectroscopy device and a first motion state of the patient via the electromyography device while the initial amount of training is set as the set amount of training and the patient moves the paralyzed part according to the first image;
- determine a spasticity state of the paralyzed part of the patient when the first brain activity is equal to or less than the initial brain activity and the first motion state is more than the initial motion state;
- reduce the set amount of training to a first amount of training when the processor determines the spasticity state of the paralyzed part of the patient;
- display the second image on the head-mounted display when the processor determines the spasticity state of the paralyzed part of the patient, the second image corresponding to the first amount of training of the paralyzed part so as to encourage the patient to move the paralyzed part according to the second image, a motion speed of the second image being slower than a motion speed of the first image;
- increase the set amount of training to a second amount of training when the processor does not determine the spasticity state of the paralyzed part of the patient;
- display the third image on the head-mounted display when the processor does not determine the spasticity state of the paralyzed part of the patient, the third image corresponding to the second amount of training of the paralyzed part so as to encourage the patient to move the paralyzed part according to the third image, a motion speed of the third image being faster than the motion speed of the first image; and
- stop the training when the processor determines that the set amount of training is finished by the patient.

* * * * *